United States Patent [19]

Katayama et al.

[11] Patent Number: 4,923,586
[45] Date of Patent: May 8, 1990

[54] ENZYME ELECTRODE UNIT

[75] Inventors: Hideo Katayama, Kusatsu; Yoshiaki Yoshida, Ikoma; Tatsuhiko Osaka, Kurita, all of Japan

[73] Assignee: Daikin Industries, Ltd., Osaka, Japan

[21] Appl. No.: 407,672

[22] Filed: Sep. 14, 1989

Related U.S. Application Data

[63] Continuation of Ser. No. 176,281, Mar. 31, 1988, abandoned.

[30] Foreign Application Priority Data

Mar. 31, 1987 [JP] Japan .................................. 62-80431
Mar. 31, 1987 [JP] Japan .................................. 62-80433

[51] Int. Cl.$^5$ ............................................. C12M 1/34
[52] U.S. Cl. ................................... 204/403; 435/291; 435/817
[58] Field of Search ................ 435/817, 291; 204/1 E, 204/403

[56] References Cited

U.S. PATENT DOCUMENTS

| | | | |
|---|---|---|---|
| 4,073,713 | 2/1978 | Newman | 435/817 X |
| 4,388,166 | 6/1983 | Suzuki et al. | 204/403 |
| 4,404,066 | 9/1983 | Johnson | 204/1 T |

Primary Examiner—G. L. Kaplan
Attorney, Agent, or Firm—Beveridge, DeGrandi & Weilacher

[57] ABSTRACT

An enzyme electrode unit having, on the surfaces of the base electrodes thereof, an enzyme-immobilized membrane for oxidizing or reducing a target substance to be measured, and a diffusion-limiting membrane unit of a two-layer structure disposed on the surface of the enzyme-immobilized membrane, only the diffusion-limiting membrane having a lower target substance diffusion limiting effect being replaceable, thus maintaining substantially constant the general target substance diffusion limiting effect of the diffusion-limiting membrane unit, even after the replaceable diffusion-limiting membrane has been replaced.

13 Claims, 5 Drawing Sheets (PLAIN CELLOPHANE + POLYCARBONATE MEMBRANE)

(CELLOPHANE ONLY)

ENZYME ELECTRODE UNIT

This application is a continuation, of application Ser. No. 176,281, filed Mar. 31, 1988, now abandoned.

BACKGROUND OF THE INVENTION

The present invention relates to an enzyme electrode unit, and more particularly to an enzyme electrode unit in which diffusion-limiting membranes limit the diffusion of a target substance to be measured and the substance as limited in diffusion is guided to an enzyme-immobilized membrane.

It is known that a physiologic active substance has a characteristic capable of selectively detecting a very complicated organic compound, protein or the like with high sensitivity. With attention directed to this characteristic, researches and developments have been made on measurement of such organic compound, protein or the like with the use of an enzyme electrode unit having base electrodes on which a physiologic active substance is immobilized.

When measuring a target substance with the use of the enzyme electrode unit above-mentioned, the target substance is oxidized or reduced by the enzyme immobilized on the surfaces of the base electrodes. By measuring the concentration of the oxygen, hydrogen peroxide or the like which undergoes a change by such oxidation or reduction, the concentration of the target substance can be indirectly measured.

For example, when the concentration of glucose is to be measured, glucose oxidase (hereinafter referred to as GOD) may be used as a physiologic active substance. In this case, the following reaction takes place:

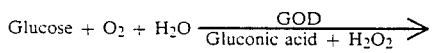

Accordingly, the concentration of glucose can be determined by detecting the decrease in oxygen concentration or the increase in hydrogen peroxide concentration.

More specifically, an enzyme-immobilized membrane having enzyme immobilized on an acetylcellulose membrane is stuck to the surfaces of hydrogen peroxide electrodes used as the base electrodes, and a polycarbonate membrane covers the enzyme-immobilized membrane. To enhance the sensitivity of measuring the concentration of glucose, the total thickness of both membranes is set to 10 μm.

In the example above-mentioned, the total membrane thickness is extremely thin in order to enhance the concentration measuring sensitivity. Consequently, the solution is guided to the enzyme-immobilized membrane with the glucose concentration being extremely high. Further, as apparent from the reaction formula mentioned earlier, the glucose concentration measuring limit is determined according to the amount of oxygen contained in a target solution to be measured. As a result, the glucose concentration measuring limit is very low. In this connection, if it is intended to increase the glucose concentration measuring limit, it is required to previously dilute the glucose solution at a predetermined dilution ratio. This causes the dilution mechanism to be complicated, and requires an expensive dilution apparatus.

To overcome such problems, it has been proposed, as disclosed in the Japanese Laid-Open Patent Publication No. 59-22620, that a diffusion-limiting membrane for limiting the diffusion of glucose is disposed instead of the polycarbonate membrane to increase the glucose concentration measuring limit without dilution of a glucose solution.

The description hereinbefore which has discussed mainly the case of measuring the concentration of glucose, may be also applied to the case of measuring the concentration of other organic macromolecule, protein or the like.

In the enzyme electrode unit above-mentioned, when a solution containing a target substance to be measured also contains interfering substances having a large particle diameter, the diffusion-limiting membrane not only restricts the diffusion of the target substance to be measured, but also prevents the interfering substances from penetrating therethrough. This assures an accurate measurement of a wide range of concentrations of a target substance to be measured.

Upon completion of one measurement as above-mentioned, a relatively great amount of interfering substances stick to the diffusion-limiting membrane. This inevitably reduces that portion of the diffusion-limiting membrane which achieves a predetermined diffusion limitation for the target substance to be measured. Therefore, the diffusion-limiting membrane as it is, cannot assure an accurate measurement on and after the second operation. Accordingly, it is a common practice that, after a predetermined number of measurements has been made, preferably after every measurement has been made, the diffusion-limiting membrane is exchanged with a new one to achieve measurement without any influence of the interfering substances. If there are neither variations in the characteristics of the replaced diffusion-limiting membranes themselves, nor variations in diffusion-limiting membrane mounting condition, an accurate measurement can be assured with the influence of the interfering substances eliminated after the replacement of diffusion-limiting membrane.

However, it is not assured at all that such variations are absent. Generally, there exist not only considerable variations in the characteristics of diffusion-limiting membranes themselves, but also considerable variations in membrane mounting condition. Accordingly, even though the influence of the interfering substances can be eliminated, such variations may produce considerable variations in measured results.

Further, the membrane mounted on the base electrodes is extremely thin, requiring extreme care to be used when handling the membrane.

It may be proposed that the diffusion-limiting membrane is mounted on a cap or the like in consideration of its removal, and the diffusion-limiting membrane is adapted to be automatically stuck to the enzyme-immobilized membrane when such cap is secured to the electrode unit body, threadedly or in other manner.

If a diffusion-limiting membrane is mounted in such manner, the membrane has a limited portion for which physical adhesion is assured. Accordingly, when a plurality of measurements are made even without replacement of the diffusion-limiting membrane, the measured data may considerably vary.

More specifically, when no measurement is still made, the enzyme-immobilized membrane is held wet and the diffusion-limiting membrane is also held wet. However, since no excessive electrode conserving liquid is present, the adhesion of the enzyme-immobilized membrane to the diffusion-limiting membrane is assured fairly well throughout the surfaces. However, when measurement starts by dropping a target solution to be measured on the diffusion-limiting membrane or by dipping the enzyme electrode unit in such solution, both membranes become excessively wet due to the target solution to be measured. Accordingly, it is considered that the adhesion of both membranes at other portions thereof than those to which a physical pressing force is directly applied, may be destroyed under the influence of surface tension or the like. It is also considered that the adhesion of both membranes may be destroyed under the influence of target solution dropping conditions or conditions of dipping the enzyme electrode unit in the target solution. The extent to which the adhesion of both membranes is destroyed, varies in each measurement, resulting in variations in measured data as above-mentioned.

Further, the diffusion-limiting membrane itself is very thin. This requires extreme care to be used when replacing or handling the membrane.

SUMMARY OF THE INVENTION

It is an object of the present invention to provide an enzyme electrode unit capable of eliminating the influence of interfering substances and considerably reducing the influence of variations resulting from the replacement of a diffusion-limiting membrane.

It is another object of the present invention to provide an enzyme electrode unit capable of reducing variations in conditions of mounting a diffusion-limiting membrane on an enzyme-immobilized membrane.

It is a further object of the present invention to provide an enzyme electrode unit in which the membranes to be mounted on the base electrodes are easy to handle.

In order to achieve the objects above-mentioned, the enzyme electrode unit in accordance with the present invention has base electrodes for supplying an electric signal corresponding to the amount of substance produced or consumed by a physiologic active substance, and comprises;
- an enzyme-immobilized membrane in/on which the physiologic active substance is immobilized, secured to the surfaces of the base electrodes;
- a first diffusion-limiting membrane having a higher diffusion limiting effect secured to the surface of the enzyme-immobilized membrane; and
- a second diffusion-limiting membrane having a lower diffusion limiting effect removably disposed on the surface of the first diffusion-limiting membrane.

Preferably, the enzyme-immobilized membrane has an obverse to which the first diffusion-limiting membrane is stuck and secured, and a reverse to which stuck and secured is a selective penetration membrane through which the produced or consumed substance selectively penetrates.

According to the present invention, a target substance to be measured in a solution is guided to the enzyme-immobilized membrane with the diffusion of the substance limited by the first and second diffusion-limiting membranes, i.e., with the concentration of the target substance lowered at a predetermined rate. Then, there may be generated an electric signal corresponding to the concentration of the target substance to be measured which has penetrated through the diffusion-limiting membranes. Accordingly, the influence of interfering substances may be eliminated and the concentration measuring limit may be increased corresponding to the diffusion limiting effect to the target substance to be measured.

When the second diffusion-limiting membrane is replaced, there may exist variations in the characteristics of the second diffusion-limiting membrane itself, as well as variations in conditions of mounting the second diffusion-limiting membrane. In spite of such variations, the general limiting effect of the first and second diffusion-limiting membranes may be maintained substantially constant. Further, the influence of interfering substances may be effectively eliminated, thus assuring an accurate measurement of the concentration of a target substance to be measured.

More specifically, the general penetration ratio P of a unit of the first and second diffusion-limiting membranes in its entirety, is expressed by the following equation:

$$P = P1P2/(P1+P2),$$

where
- P1 is the penetration ratio of the first diffusion-limiting membrane (this is a value which is obtained by dividing the diffusion coefficient by the membrane thickness and which is inversely proportional to the diffusion limiting effect), and
- P2 is the penetration ratio of the second diffusion-limiting membrane.

Since P2 is much greater than P1 (P2>>P1), the general penetration ratio P undergoes no substantial change even though the penetration ratio P2 varies more or less. Accordingly, even if the second diffusion-limiting membrane is replaced in order to eliminate the influence of obstructive substances, the general diffusion limiting effect may be maintained substantially constant. Thus, an accurate measurement of concentration may be assured.

When the enzyme-immobilized membrane has an obverse to which the first diffusion-limiting membrane is stuck and secured, and a reverse to which stuck and secured is the selective penetration membrane through which the produced or consumed substance above-mentioned selectively penetrates, it is possible to eliminate the influence of the surface tension of a target solution to be measured, the influence of conditions of such solution and the like, enabling to obtain measured data with extremely small variations.

All the membranes are held together as a unit, facilitating the manipulation of the membranes.

Other objects, advantages and novel characteristics of the present invention will be apparent from the following description.

BRIEF DESCRIPTION OF THE DRAWINGS

FIG. 2 (B) shows measured data obtained with the use of a comparative example of an enzyme electrode unit;

DESCRIPTION OF THE PREFERRED EMBODIMENTS

Figure 1:
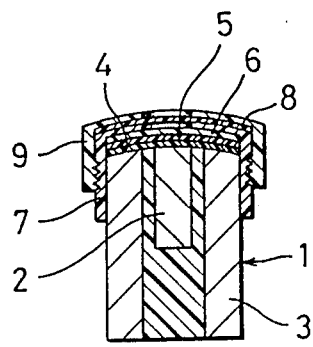
FIG. 1 is a longitudinal section view of an enzyme electrode unit in accordance with a first embodiment of the present invention.

FIG. 1 is a longitudinal section view of the enzyme electrode unit in accordance with a first embodiment of the present invention.

The enzyme electrode unit includes: a rod-like member 1 made of an insulating material; a center electrode made of Pt and an opposed electrode 3 made of Ag, both electrodes 2 and 3 being disposed at one surface of the rod-like member 1; a hydrogen peroxide selective penetration membrane 4; a GOD immobilized membrane 5; a first diffusion-limiting membrane 6; and a cap 7 for securing these membranes 4, 5 and 6. The membranes 4, 5 and 6 are laminated on one another as if covering that surface of the rod-like member 1 at which both electrodes 2 and 3 are disposed. A second diffusion-limiting membrane 8 is laminated on the first diffusion-limiting membrane 6 with the use of a screw cap 9.

When measuring the concentration of glucose with use of the enzyme electrode unit having the arrangement above-mentioned, it is required to apply a predetermined bias voltage across the center electrode 2 and the opposed electrode 3. In this connection, an electrode bias device shown in FIG. 3 is used.

Figure 3:
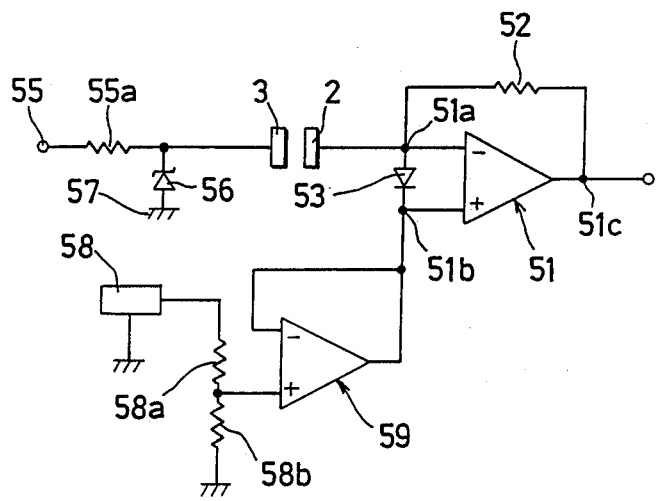
FIGS. 3 and 4 are electric circuit diagrams of electrode bias devices applied to the enzyme electrode unit in accordance with the present invention, respectively.

FIG. 3 is an electric circuit diagram of a first example of the electrode bias device.

In the electrode bias device in FIG. 3, a current/voltage converting resistance 52 is connected between an output terminal 51c and an inverting input terminal 51a of a current/voltage converting operational amplifier 51, and a diode 53 is connected between the inverting input terminal 51a and a non-inverting input terminal 51b of the operational amplifier 51 such that the anode of the diode 53 is connected to the inverting input terminal 51a. The inverting input terminal 51a is connected to the center electrode 2 used as an anode-side electrode. The opposed electrode 3 used as a cathode electrode is connected to a reverse bias voltage supply terminal 55 through resistance 55a, and is also connected to grounding 57 through a Zener diode 56. An output voltage from a constant voltage supply source 58 is divided by resistances 58a, 58b, and the voltage thus divided is supplied to the non-inverting input terminal 51b through a buffer amplifier 59. In the example above-mentioned, since the hydrogen peroxide selective penetration membrane 4 is used, the center electrode 2 is used as an anode-side electrode while the opposed electrode 3 is used as a cathode-side electrode. If an oxygen selective penetration membrane is used instead of the hydrogen peroxide selective penetration membrane 4, the center electrode 2 will be used as a cathode-side electrode while the opposed electrode 3 will be used as an anode-side electrode.

The following description will discuss the electrode bias operation carried out by the electrode bias device having the arrangement above-mentioned.

For measuring the concentration of glucose, a voltage of 0 V may be supplied from the reverse bias voltage supply terminal 55, causing the opposed electrode 3 to be grounded.

More specifically, the constant voltage supply source 58 always generates a predetermined voltage, which is divided by the resistances 58a, 58b (the divided voltage is set to 0.9 V for the Pt-Ag electrodes). The divided voltage is supplied to the non-inverting input terminal 51b of the current/voltage converting operational amplifier 51 through the buffer amplifier 59. Therefore, a reverse bias voltage is applied to the diode 53. Thus, the divided voltage is applied to the center electrode 2 through the inverting input terminal 51a by virtual grounding between the inverting and non-inverting input terminals of the current/voltage converting operational amplifier 51. That is, a forward bias voltage is applied across the center electrode 2 and the opposed electrode 3.

In such forward bias state, a current corresponding to the amount of hydrogen peroxide produced by the reaction of glucose under the presence of the GOD immobilized on the GOD immobilized membrane 5, flows from the center electrode 2 to the opposed electrode 3. Since the diode 53 is non-conductive, there can be taken out, from the output terminal 51c of the current/voltage converting operational amplifier 51, a voltage signal in which an offset voltage generated by the forward bias voltage is being superposed on the voltage signal proportional to the current above-mentioned.

By supplying the voltage signal thus taken out to a differentiation circuit (not shown), the amount of voltage variation proportional to the amount of output current variation can be obtained. Through a predetermined operation of the amount of voltage variation thus obtained, there is obtained the amount of output current variation which corresponds to the glucose concentration.

It is known that, after the glucose concentration measuring operation above-mentioned has been made, the oxidative reaction forms an oxide layer on the electrode surfaces to decrease the level of a signal taken out, assuring no accurate measurement of glucose concentration. To prevent such decrease in signal level to assure an accurate measurement of glucose concentration, a bias voltage having a reversed polarity may be applied across the center electrode 2 and the opposed electrode 3, thus removing the oxide layer above-mentioned.

To carry out such oxide layer removing operation, a voltage (for example, 5 V) higher than the divided voltage may be supplied from the reverse bias voltage supply terminal 55.

More specifically, the divided voltage is supplied to the non-inverting input terminal 51b of the current-/voltage converting operational amplifier 51 as done in the forward bias state. Therefore, a reverse bias voltage is applied across the center electrode 2 and the opposed electrode 3 through the Zener diode 56 (The reverse bias voltage is 1.2 V with the voltage across the diode 53 terminals or the like taken into account).

In the reverse bias state, a current flows from the opposed electrode 3 to the center electrode 2. When, with the increase in current, the output from the current/voltage converting operational amplifier 51 is saturated such that a voltage of the inverting input terminal 51a becomes greater than a voltage of the non-inverting input terminal 51b, a forward bias voltage is applied to the diode 53, causing the same to be conductive. Accordingly, a refresh current is bypassed by the diode 53. With a predetermined reverse bias voltage applied across the center electrode 2 and the opposed electrode 3, a sufficient amount of a current flows therebetween, assuring a reliable refreshment operation.

Thereafter, a predetermined forward bias voltage is applied across the center electrode 2 and the opposed electrode 3 as mentioned earlier, whereby an accurate measurement of glucose concentration can be made without influence of an oxide layer.

An example of the enzyme electrode unit according to the present invention was formed. As the first diffusion-limiting membrane 6, plain cellophane (type: #300) manufactured by Futamura Kagaku Kogyo Co., Ltd. was used. As the second diffusion-limiting membrane 8, there was used a polycarbonate membrane manufactured by Nuclepore Corp. (bore diameter: 0.05 $\mu$m, standard bore density: $6 \times 10^8$ pores/cm$^2$, flow amount of nitrogen: 0.8 liter/min/cm$^2$ (10 psi), membrane thickness: 5 $\mu$m).

Figure 2:
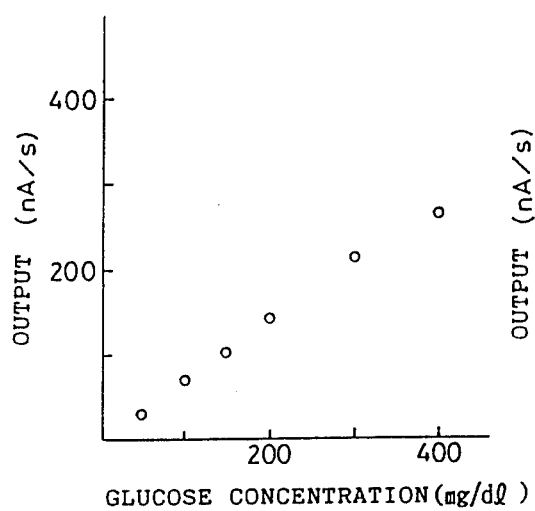
FIG. 2 (A) shows measured data obtained with the use of the enzyme electrode unit in FIG. 1.
Figure 2:
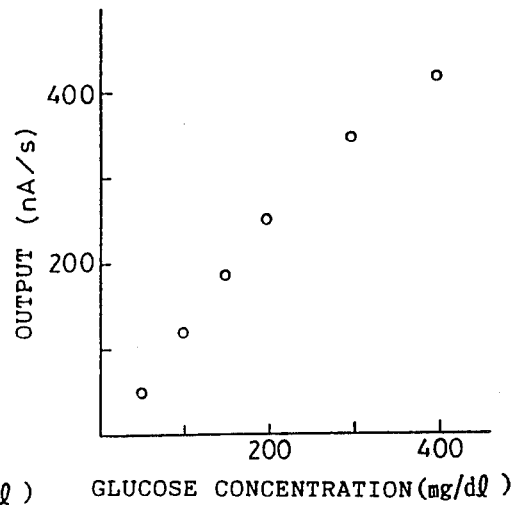

With a bias voltage applied to the enzyme electrode unit having the arrangement above-mentioned, measurements of glucose concentration were made. FIG. 2 (A) shows the characteristics of the output current variations/glucose concentrations obtained as the result of such measurements. As a comparative example, measurements of glucose concentration were made with an enzyme electrode unit using a diffusion-limiting membrane made of cellophane only. FIG. 2 (B) shows the characteristics of the output current variations/glucose concentrations obtained as the result of such measurements. In the comparative example in FIG. 2 (B), the output currents corresponding to the same glucose concentrations are about twice those in the Example in FIG. 2 (A). Accordingly, the enzyme electrode in accordance with the present invention may have a higher measuring limit of glucose concentration than that of the comparative example.

With the use of the enzyme electrode having the arrangement above-mentioned of the present invention, a solution having a glucose concentration of 150 mg/dl was measured with the second diffusion-limiting membrane 8 replaced for each measurement. The following table shows the variations of output current in such measurements. As a comparative example, with the use of an enzyme electrode having one cellophane diffusion-limiting membrane, a solution having a glucose concentration of 150 mg/dl was measured with the cellophane replaced for every measurement. The output current variations in the comparative example are also shown in the following table.

TABLE

| | Number of times | | | | | | | | | |
|---|---|---|---|---|---|---|---|---|---|---|
| | 1 | 2 | 3 | 4 | 5 | 6 | 7 | 8 | 9 | 10 |
| Example (nA/s) | 122 | 120 | 120 | 124 | 125 | 119 | 123 | 121 | 122 | 120 |
| Comparative Example (nA/s) | 162 | 207 | 191 | 186 | 216 | 223 | 170 | 218 | 220 | 221 |

As apparent from the Table, the average of the output current variations in the Example is 122 nA/s, which is considerably small as compared with the average 200 nA/s in the Comparative Example. However, the variation throughout 10 measurements in the Example is 1.6%, which is considerably reduced as compared with the variation 10.9% in the Comparative Example. Accordingly, the Example considerably reduces the variations in the general diffusion limiting effect accompanied by the replacement of the second diffusion-limiting membrane 8, thus achieving a stable measurement of glucose concentration.

In particular, when measuring the glucose concentration in blood, macromolecules such as albumen, blood corpuscles, enzyme or the like may be stuck to the second diffusion-limiting membrane 8, causing the same to get clogged. This requires replacement of the second diffusion-limiting membrane 8 for each measurement. Even under such conditions, the present invention assures a highly stable measurement.

In the embodiment above-mentioned, the diffusion-limiting membrane unit has a two-layer structure, of which only one diffusion-limiting membrane presenting a smaller diffusion limiting effect is replaceable. Accordingly, even though such diffusion-limiting membrane is replaced, the general diffusion limiting effect can be maintained substantially constant. This not only assures a stable measurement of the concentrations of a target substance, but also considerably reduces damages to the enzyme-immobilized membrane resulting from the replacement of diffusion-limiting membrane. Further, the replaceable diffusion-limiting membrane may have a thickness which enables the membrane to be easily wetted. This permits the replaceable diffusion-limiting membrane to be preserved in a dry condition.

Moreover, the use of the electrode bias device mentioned earlier assures an accurate measurement of a target substance with the application of a forward bias voltage suffering no change by external factors. Further, the diode is disposed to eliminate the influence of saturation of the current/voltage converter with the application of a reverse bias voltage for refreshment. A sufficient amount of a refreshment current can let flow with the application of a reverse bias voltage suffering no change by external factors.

It was also found that, with the use of normal cellophane (Type: #300) manufactured by Tokyo Cellophane Paper Co., Ltd. as the first diffusion-limiting membrane 6, a stable measurement of glucose concentrations was made.

Figure 4:
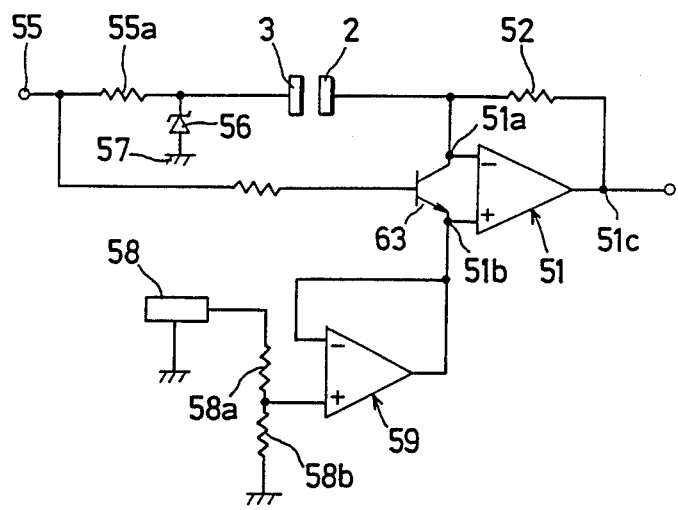

FIG. 4 shows an electric circuit diagram of a second example of the electrode bias device. The second example is the same as the first example device in FIG. 3, except that a switching transistor 63 of the npn type is used instead of the diode 53 in FIG. 3, and the base terminal of the switching transistor 63 is connected to a reverse bias voltage supply terminal 55 through resistance.

With such arrangement, the status of the switching transistor 63 is forcibly controlled according to a voltage of the reverse bias voltage supply terminal 55.

More specifically, when a voltage of 0 V is supplied from the reverse bias voltage supply terminal 55, the switching transistor 63 becomes non-conductive. Accordingly, a predetermined forward bias voltage can be applied across the center electrode 2 and the opposed electrode 3, as in the first example in FIG. 3. In such state, glucose concentrations can be measured.

On the contrary, when the reverse bias voltage supply terminal 55 supplies a voltage higher than a divided voltage, the switching transistor 63 becomes conductive. A predetermined reverse bias voltage is applied across the center electrode 2 and the opposed electrode 3 as in the electrode bias device in FIG. 3. In such state, the enzyme electrode unit can be refreshed.

In the electrode bias device having the arrangement in FIG. 4, a pnp-type switching transistor or a field-effect transistor may be used instead of the npn-type switching transistor 63.

Figure 5:
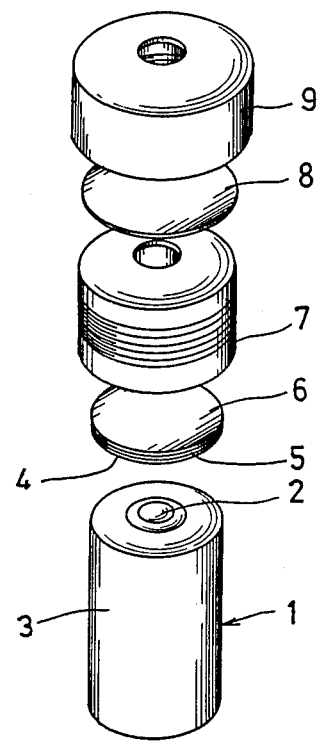
FIG. 5 is an exploded perspective view of an enzyme electrode unit in accordance with a second embodiment of the present invention.

FIG. 5 is an exploded perspective view of a second embodiment of the enzyme electrode unit in accordance with the present invention.

The second embodiment is the same as the first embodiment in FIG. 1, except that a hydrogen peroxide selective penetration membrane 4, a GOD immobilized membrane 5 and a first diffusion-limiting membrane 6 are laminated on and securely stuck to one another.

More specifically, the hydrogen peroxide selective penetration membrane 4 is stuck and secured to the GOD immobilized membrane 5 by a casting membrane method, and the diffusion-limiting membrane 6 is stuck and secured to the GOD immobilized membrane 5 by chitosan. The membranes may be stuck and secured in other manner than that above-mentioned, as far as the membranes can be sufficiently stuck and secured to one another.

With the use of the enzyme electrode unit having the arrangement in FIG. 5, a glucose concentration can be measured with higher stability.

More specifically, a second diffusion-limiting membrane 8 has a penetration ratio considerably higher than that of the first diffusion-limiting membrane 6. Accordingly, even though both diffusion-limiting membranes are not held together as a unit, the membranes are not subject to substantial influence of the glucose solution dropping conditions or the like. When the hydrogen peroxide selective penetration membrane 4, the GOD immobilized membrane 5 and the first diffusion-limiting membrane 6 are held together as a unit, these membranes are considerably less influenced by the glucose solution dropping conditions or the like than the case where these membranes are not held together as a unit.

As an Example, ten measurements of glucose concentration were made with the hydrogen peroxide selective penetration membrane 4, the GOD immobilized membrane 5 and the first diffusion-limiting membrane 6 held together as a unit and without use of the second diffusion-limiting membrane 8. The following table shows the output current variations obtained in such measurements. As a Comparative Example, ten measurements of glucose concentration were made with the use of an enzyme electrode unit in which a diffusion-limiting membrane 6 is secured to the GOD immobilized membrane 5 by a cap.

TABLE

| | Number of times | | | | | | | | | |
|---|---|---|---|---|---|---|---|---|---|---|
| | 1 | 2 | 3 | 4 | 5 | 6 | 7 | 8 | 9 | 10 |
| Example (nA/s) | 155 | 152 | 151 | 152 | 152 | 151 | 154 | 152 | 152 | 152 |
| Comparative Example (nA/s) | 157 | 168 | 169 | 171 | 169 | 169 | 174 | 175 | 181 | 179 |

As apparent from the Table, the average of measured data is 152 nA/s where the hydrogen peroxide selective penetration membrane 4, the GOD immobilized membrane 5 and the first diffusion-limiting membrane 6 were laminated and held together as a unit. This value is smaller than the average 171 nA/s in the Comparative Example. However, the variation in the measured data in the Example is 0.82%, which shows a considerable improvement in stability of measured data as compared with the variation of 3.9% in the Comparative Example.

As apparent from the second embodiment, the hydrogen peroxide selective penetration membrane 4, the GOD immobilized membrane 5 and the first diffusion-limiting membrane 6 are laminated and held together as a unit. Accordingly, a stable measurement can be assured without influences of the surface tension of a glucose solution, the glucose solution dropping conditions, the glucose solution dipping conditions and the like.

Figure 6:
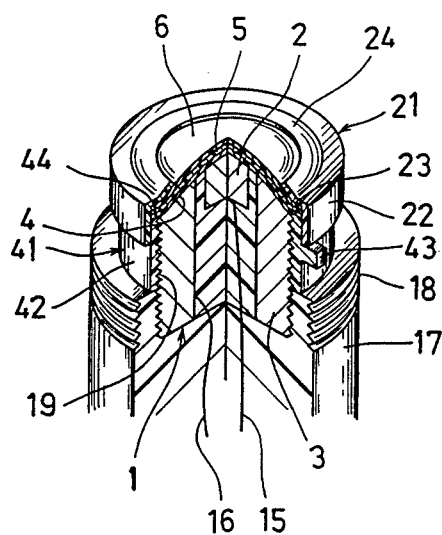
FIG. 6 is a perspective view, with portions broken away, illustrating how an GOD immobilized membrane is mounted on the electrode unit of the present invention.

FIG. 6 is a perspective view, with portions broken away, of an example of an enzyme electrode unit in which a hydrogen peroxide selective penetration membrane, a GOD immobilized membrane and a first diffusion-limiting membrane are laminated and held together as a unit. This enzyme electrode unit includes: a rod-like member 1 having a center electrode 2 and an opposed electrode 3; a hydrogen peroxide selective penetration membrane 4; a GOD immobilized membrane 5; a first diffusion-limiting membrane 6; a cap-like support member 21; and an undercap 41 fitted in the cap-like support member 21.

The rod-like member 1 has a hollow casing 17 made of an insulating material such as synthetic resin. Lead lines 15, 16 are secured to the inside of the casing 17 by filling the same with insulating adhesives or the like. The center electrode 2 and the opposed electrode 3 are embedded in and secured to one end surface of the rod-like member 1. The opposed electrode 3 is provided in the outer surface thereof with an external thread 19, with the use of which the undercap 41 is mounted. The casing 17 is provided with an external thread 18 in the outer surface at the electrode mounting side thereof.

The center electrode 2 and the opposed electrode 3 are coaxial. The rod-like member 1 has a convex curved surface (having the radius of curvature of, for example, 10 mmR) at its end surface to which the center electrode 2 and the opposed electrode 3 are secured.

Figure 7:
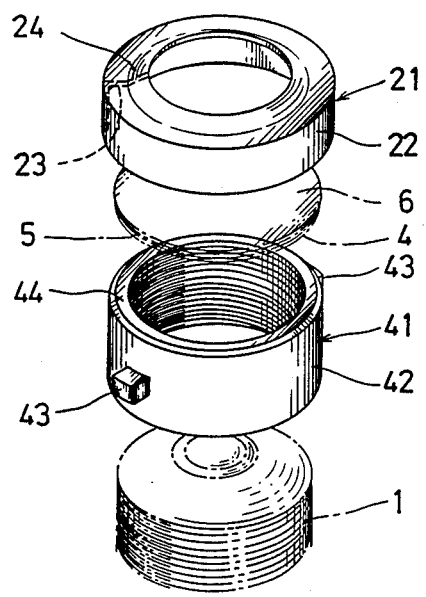
FIG. 7 is an exploded perspective view showing the relationship between an undercap and a cap-like support member.

As shown in FIG. 7, the undercap 41 has a casing 42 made of polyacetal resins, which is provided at a predetermined position of its external periphery with a projection 43 for controlling the fitting amount of the cap-like support member 21. The undercap 41 has a GOD immobilized membrane holding surface 44 at the upper end surface thereof.

As shown in FIG. 7, the cap-like support member 21 has a casing body 22 made of polyacetal resins of which inner diameter is the same as the outer diameter of the casing 42. The casing body 22 is provided at the upper end thereof with an inwardly turned collar integral therewith. The inwardly turned collar has a width greater than that of the GOD immobilized membrane holding surface 44 of the undercap 41. That portion of the inwardly turned collar which is opposite to the GOD immobilized holding surface 44, serves as a GOD immobilized holding surface 23. That portion of the inwardly turned collar which is positioned at the inner part with respect to the GOD immobilized holding surface 23, serves as a flange 24. The collar is generally made thin such that the flange 24 can be deformed along the convex curved surface of the rod-like member 1 when the cap-like support member 21 is fitted to the undercap 41.

Figure 8:
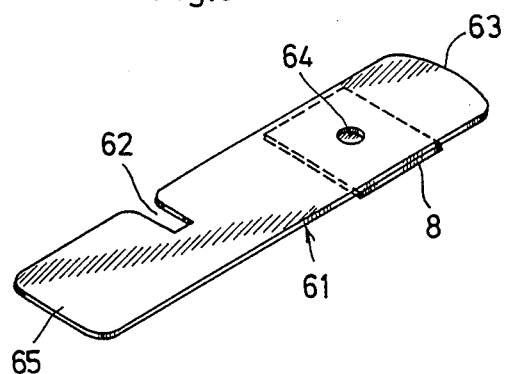
FIG. 8 is a perspective view illustrating a diffusion-limiting membrane holding means on which a second diffusion-limiting membrane is mounted.
Figure 9:
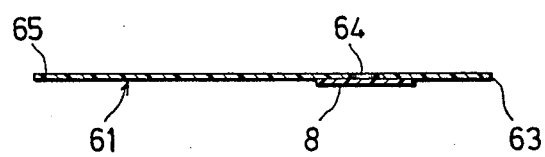
FIG. 9 is a vertical section view of the center portion of the means in FIG. 8.

FIG. 8 is a perspective view of diffusion-limiting membrane holding means on which the second diffusion-limiting membrane 8 is mounted, and FIG. 9 is a vertical section view of the center portion of the means in FIG. 8.

This means has a relatively resilient thin plate 61 substantially in the form of a rectangle which has resistance against a target solution to be measured. The plate 61 has a square engagement concave 62 at the center of one of the longer sides thereof. One shorter side 63 is arcuate. The plate 61 has a circular opening 64 of which center is positioned at the center of a circle including the arc. The second diffusion-limiting membrane 8 is attached to the underside of the thin plate 61 with adhesives or by other suitable means, such that the opening 64 is covered by this membrane 8. That portion of the thin plate 61 which is close to the other shorter side, serves as a holding portion 65.

As shown in FIG. 6, with the undercap 41 mounted on the rod-like member 1, the integrally laminated membrane unit of the hydrogen peroxide selective penetration membrane 4, the GOD immobilized membrane 5 and the first diffusion-limiting membrane 6 is placed on the convex curved surface of the rod-like member 1. Then, the cap-like support member 21 is fitted to the undercap 41, causing the integrally laminated membrane unit to be stuck to the convex curved surface of the rod-like member 1.

More specifically, in the middle course of fitting the cap-like support 21 to the undercap 41, the integrally laminated membrane unit is held by and between the inner peripheral edge of the flange 24 and the convex surface of the rod-like member 1. At this time, at least the center portion of the integrally laminated membrane unit is stuck to the convex surface of the rod-like member 1. However, it is not assured that the peripheral portion of the membrane unit is entirely stuck to the peripheral portion of the rod-like member 1. Generally, the membranes become more or less creased. When fitting the cap-like support member 21 is continued, the flange 24 is deformed along the convex surface of the rod-like member 1. The point of the flange 24 which holds the integrally laminated membrane unit together with the holding surface 44, is gradually moved outward. The creases produced at the peripheral portions of the membranes are thus removed. Finally, that portion of the integrally laminated membrane unit which is positioned at the inner side with respect to the flange 24, is completely stuck to the convex surface of the rod-like member 1. Creases remains only on those portions of the membranes which come in contact with the GOD immobilized membrane holding surface 23 and the flange 24.

Figure 10:
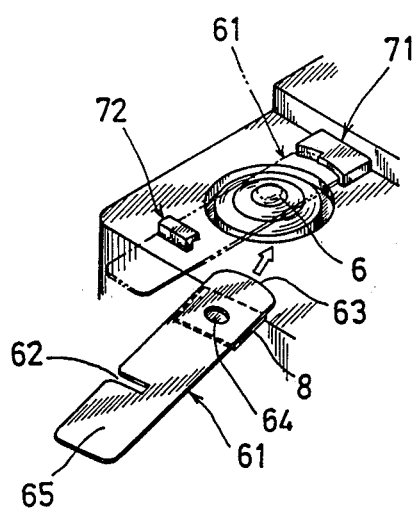
FIG. 10 is a schematic perspective view illustrating a mechanism for positioning the diffusion-limiting membrane holding means in FIG. 8.

Then, the second diffusion-limiting membrane 8 mounted on the thin plate 61 is stuck to the first diffusion-limiting membrane 6, as shown in FIG. 10. This enables to maintain substantially constant the general diffusion limiting effect of both diffusion-limiting membranes 6 and 8, thus assuring an accurate measurement of glucose concentration.

More specifically, the enzyme electrode unit is mounted at a predetermined position on a base stand of a measuring apparatus with the electrode surfaces projecting upward. The base stand has engagement portions 71, 72 opposite to each other with the enzyme electrode unit put therebetween. After said one shorter side 63 of the thin plate 61 has been engaged with the engagement portion 71, the holding portion 65 may be engaged with the engagement portion 72 by rotating the thin plate 61 with the holding portion 65 held with the hand. The thin plate 61 is curved, causing the second diffusion-limiting membrane 8 to be stuck to the first diffusion-limiting membrane 6.

With the use of the mounting mechanism having the arrangement above-mentioned, 100 measurements were made of a glucose solution of which concentration is 150 mg/dl. The variation in measured data was 3.2%, which demonstrates that the glucose concentration measurements were made with high precision.

If the enzyme electrode unit has not been used for glucose concentration measurement or has been preserved for a long period of time to decrease the activity of the GOD immobilized membrane 5, the second diffusion-limiting membrane 8 may be removed and the integrally laminated membrane unit may be removed together with the cap-like support member 21. Then, a new integrally laminated membrane unit may be mounted under tension with the the use of the cap-like support member 21, and the diffusion-limiting membrane 8 may be mounted again. Thereafter, a good glucose concentration measurement may be assured.

When the mounting mechanism above-mentioned is used, it is possible to entirely stick that portion of the integrally laminated membrane unit which is exposed outside, to the convex surface of the rod-like member throughout the unit surface by merely mounting the cap-like support member 21. This results in improvements in accuracy of a glucose concentration measurement.

The application of the mounting mechanism above-mentioned is not limited to that for mounting an integrally laminated membrane unit, but this mechanism may be also used for mounting membranes which are not integrally laminated and held as a unit.

Instead of the hydrogen peroxide selective penetration membrane 4, an oxygen selective penetration membrane may be used. In such case, a glucose concentration may be measured based on the amount of oxygen consumed as a result of an enzyme reaction.

The embodiments have been discussed in connection with measurement of glucose concentration. However, instead of the GOD immobilized membrane, there may be used an enzyme-immobilized membrane on which another physiologic active substance than glucose oxidase is immobilized. In such case, concentration measurement of other organic macromolecule, protein or the like may be made.

With the use of the diffusion-limiting membrane holding means in which the second diffusion-limiting membrane 8 is mounted on the thin plate 61, the second diffusion-limiting membrane 8 may be mounted on the enzyme electrode unit in FIG. 1.

What is claimed is:

1. An enzyme electrode unit, comprising:
   an enzyme-immobilized membrane;
   a first diffusion-limiting membrane having a first target substance diffusion limiting effect, said first membrane being secured to the surface of said enzyme-immobilized membrane;
   a second diffusion-limiting membrane having a target substance diffusion limiting effect which is lower than said first target substance diffusion limiting effect;
   first holding means for holding in place said first diffusion-limiting membrane and said enzyme-immobilized membrane; and
   second holding means for holding said second diffusion-limiting membrane in a releasably disposed manner on a surface of said first diffusion-limiting membrane 2. An enzyme electrode unit as set forth in claim 1, wherein each of said diffusion-limiting membranes has a penetration ratio, and the penetration ratio of the second diffusion-limiting membrane is greater than the penetration ratio of the first diffusion-limiting membrane.

3. An enzyme electrode unit as set forth in claim 1, wherein the second diffusion-limiting membrane prevents substances having a particle diameter greater than that of a target substance to be measured, from penetrating therethrough.

4. An enzyme electrode unit as set forth in claim 1, wherein said second holding means is a plastic cap.

5. An enzyme electrode unit as set forth in claim 1, wherein the enzyme-immobilized membrane provokes an enzyme reaction of a target substance in blood, and the second diffusion-limiting membrane separates blood corpuscles.

6. An enzyme electrode unit as set forth in claim 1, wherein the enzyme-immobilized membrane is a membrane in/on which glucose oxidase is immobilized.

7. An enzyme electrode unit as set forth in claim 1, wherein the target substance is glucose, and the glucose diffusion limiting membrane effect of the first diffusion-limiting membrane is greater than the glucose diffusion limiting effect of the second diffusion-limiting membrane.

8. An enzyme electrode unit as set forth in claim 1, further comprising a selective penetration membrane, and wherein the enzyme-immobilized membrane is sandwiched in between said selective penetration membrane and said first diffusion-limiting membrane, and said selective penetration membrane, said enzyme-immobilized membrane and said first diffusion limiting membrane are integrally laminated and held as a unit.

9. An enzyme electrode unit as set forth in claim 8, wherein the selective penetration membrane is stuck and secured to the enzyme-immobilized membrane by a casting membrane method, and the first diffusion-limiting membrane is bonded to the enzyme-immobilized membrane.

10. An enzyme electrode unit as set forth in claim 8, wherein the selective penetration membrane is a hydrogen peroxide selective penetration membrane of hydrogen peroxide, the first diffusion-limiting membrane is a diffusion-limiting membrane of glucose, and the enzyme-immobilized membrane is a membrane in/on which glucose oxidase is immobilized.

11. An enzyme electrode unit as set forth in claim 1, wherein said second holding means is a resilient plate with an aperture formed therein.

12. An enzyme electrode unit comprising:
    an enzyme-immobilized membrane;
    a first diffusion-limiting membrane having a first target substance diffusion limiting effect, said first membrane being secured to the surface of said enzyme-immobilized membrane;
    a second diffusion-limiting membrane having a target substance diffusion limiting effect which is lower than said first target substance diffusion limiting effect;
    first holding means or holding in place said first diffusion-limiting membrane and said enzyme-immobilized membrane; and
    second holding means for holding said second diffusion-limiting membrane disposed on a surface of said first diffusion membrane, and said second holding means being releasably attached to said first holding means.

13. An enzyme electrode unit comprising:
    an enzyme-immobilized membrane;
    a first diffusion-limiting membrane having a first target substance diffusion limiting effect, said first membrane being secured to the surface of said enzyme-immobilized membrane;
    a second diffusion-limiting membrane having a target substance diffusion limiting effect which is lower than said first target substance diffusion limiting effect;
    first holding means for holding in place said first diffusion-limiting membrane and said enzyme-immobilized membrane; and
    second holding means for holding said second diffusion-limiting membrane disposed on a surface of said first diffusion membrane, and said second holding means including means for enabling the release of said second diffusion-limiting membrane from a disposed position on the surface of said first diffusion-limiting membrane while maintaining the essential integrity of said first diffusion-limiting membrane.

* * * * *